(12) United States Patent  (10) Patent No.: US 7,924,270 B2
Phelan et al.  (45) Date of Patent: Apr. 12, 2011

(54) APPARATUS AND METHOD FOR MOBILE GRAPHICAL CHEMINFORMATIC

(75) Inventors: J. Christopher Phelan, Wilmington, DE (US); David H. Silber, Wilmington, DE (US); A. James Laurino, Philadelphia, PA (US); Michael G. P. Reppy, Wilmington, DE (US)

(73) Assignee: Abacalab, Inc., Wilmington, DE (US)

( * ) Notice: Subject to any disclaimer, the term of this patent is extended or adjusted under 35 U.S.C. 154(b) by 987 days.

(21) Appl. No.: 11/347,399

(22) Filed: Feb. 6, 2006

(65) Prior Publication Data

US 2007/0192747 A1    Aug. 16, 2007

(51) Int. Cl.
*G06G 15/00* (2006.01)
(52) U.S. Cl. .................................. 345/173; 715/201
(58) Field of Classification Search .............. 703/847; 345/173, 440; 701/207; 715/512, 201
See application file for complete search history.

(56) References Cited

U.S. PATENT DOCUMENTS

| 4,870,591 | A | 9/1989 | Cicciarelli et al. |
| 6,366,293 | B1 | 4/2002 | Hamilton et al. |
| 7,250,950 | B2 * | 7/2007 | Smith et al. ................. 345/440 |
| 7,542,845 | B2 * | 6/2009 | Sands et al. .................. 701/207 |
| 2004/0263486 | A1 * | 12/2004 | Seni ............................ 345/173 |
| 2005/0125717 | A1 * | 6/2005 | Segal et al. ................. 715/512 |
| 2005/0278308 | A1 | 12/2005 | Barstow |
| 2006/0010368 | A1 | 1/2006 | Kashi |

* cited by examiner

*Primary Examiner* — Amare Mengistu
*Assistant Examiner* — Joseph G Rodriguez
(74) *Attorney, Agent, or Firm* — Connolly Bove Lodge & Hutz LLP

(57) ABSTRACT

The present invention is a pocket-sized, portable computing apparatus that performs frequently used laboratory calculations, provides a look-up function for commonly used data and procedures, and provides note-taking and data capture for record-keeping. The present invention displays data in a form that a chemist finds most convenient and manipulates this data with functions a chemist typically utilizes in his work. In addition, the present invention provides a user interface that is compatible with traditional methods for formula manipulations and chemistry workflows and that increases the efficiency of the user in performing laboratory tasks.

7 Claims, 9 Drawing Sheets

APPARATUS AND METHOD FOR MOBILE GRAPHICAL CHEMINFORMATIC

BACKGROUND OF THE INVENTION

The present invention relates generally relates to calculating apparatus and methods for chemical information and more particularly to an apparatus and method for improving the efficiency of gathering and manipulating such information in the laboratory setting.

The handling of information about chemical compounds, including recording their structures, making computations based upon the structures, and looking up structures and numerical data of compounds in reference materials, is often a time-consuming task. Chemists and other laboratory personnel working on complex chemical calculations or structures are made inefficient by the time and inconvenience associated with retrieval and processing of such information.

In addition, it is often preferable to express information about molecules or other chemical structures in graphical form. Apparatus that contain computer programs and high resolution graphic displays provide a means for the visualization of multidimensional molecular structures. These computer programs and computer models are often used by chemist and other technicians who work in a laboratory environment to better understand and predict chemical behavior. With this type of apparatus, a chemist can input a selected set of atoms and their bonds to define a chemical structure for display and analysis.

In one background art program, CS ChemDraw available from CambridgeSoft, the user initially draws the chemical structure and then can check the structure with a separate subroutine after the drawing is complete. This subroutine indicates problems with the molecular structure by highlighting. However, this program requires a computer with a desktop operating system and is limited in scope in terms of meeting the users overall laboratory needs.

Another example background art apparatus is the Lab Partner Chemistry Calculator from NuSun. The Lab Partner is a pre-programmed hand-held calculator designed specifically for chemical calculations. However, this apparatus does not allow graphical input or display of chemical formulas and structures.

Therefore, there is a need in the art to make an apparatus that has increased capability in a portable format available in the laboratory, as compared to the background art, and provide for a user's chemical data handling requirements in the laboratory and in a more user friendly application than those available in the past.

BRIEF SUMMARY OF THE INVENTION

The present invention is a pocket-sized, portable computing apparatus that performs frequently used laboratory calculations, provides a look-up function for commonly used data and procedures, and provides note-taking and data capture for record-keeping. The present invention displays data in a graphical form as a chemist finds most convenient and manipulates this data with functions a chemist typically utilizes in his work. In addition, the present invention provides a user interface that is compatible with traditional methods for formula manipulations and chemistry workflows and that increases the efficiency of the user in performing laboratory tasks.

The present invention provides a mobile, rapid and convenient means to retrieve information and perform calculations of chemical elements and chemical formulas obtained from graphical or alphanumeric entries provided by the user. In particular, the present invention provides in a form that can easily be secreted upon the user's person and transported to and used at multiple locations within and outside of the laboratory: (1) an interface for graphical entry of chemical structures and on-screen note-taking; (2) the ability to vary previously defined laboratory calculations or chemical structures; (3) a user friendly interface with, for example, step-by-step queuing and checkbox reminders for commonly performed procedures and calculations; (4) the capability to retrieve from a database information about commonly used chemicals; (5) the automatic performance of calculations without further cueing when the user enters chemical information. Further, the present invention provides simplified and efficient methods for entering graphical chemical structures, numerical, text, and procedural data.

One embodiment of the invention is an apparatus for display and analysis of chemical structures, comprising: a computing device, said computing device further comprising an operating system, chemical reaction software, graphical interface software, a plurality of types of memory and means for interfacing the computing device to a plurality of external devices; a touch-sensitive display configured to transfer touches by a stylus or other object to the software and to provide icon fields; a plurality of shortcut keys; and a navigation toggle button configured to provide easy access to the software and to control the selection of various items upon the touch screen display. In this embodiment the computing device is configured to control the software, display, plurality of shortcut keys, and navigation toggle in completing and performing computations upon a chemical reaction entered on the display.

Another embodiment of the present invention is a method for completing and performing computations upon a chemical reaction, comprising: drawing structures for a chemical reaction on a display; entering proportions, planned and measured amounts of chemicals, duration and conditions of reactions for the chemical reaction on the display; completing the chemical reaction in accordance with the chemical structures and parameters; and summarizing the data pertaining to the chemical reaction as a textual record.

Preferably, the present invention is tailored to provide easy access to the data used for chemical computations and is customized to the needs of a chemist in the laboratory. Providing this capability enables the chemist to efficiently look-up and quickly access commonly used formulas and information. In this way, the present invention provides a user-friendly interface that can reduce the workload of a chemist or other laboratory personnel and allow them to work more efficiently.

DETAILED DESCRIPTION OF PREFERRED EMBODIMENTS

The present invention uses a portable personal computer (PC) or handheld personal digital assistant (PDA) to provide an apparatus that is a versatile, portable hardware platform that is capable of efficiently executing the computer programs and computer models that implements the chemical structures and procedures of the invention. A non-limiting example of such a PDA used with the present invention would be the Axim PDA from DELL. Preferably, an example of such a PDA would include, but is not limited to: Microsoft® Windows Mobile™ 5.0 software; an Intel® XScale™ PXA270 Processor at 400 MHz or equivalent; a color TFT display in the range of 2.0" to 4.0"; a stylus to be used with the apparatus for entering graphical data; Intel 802.11b or Bluetooth™ wireless interface technology or equivalent; at least 64 MB SDRAM and 64 MB Flash ROM.

In addition, the apparatus of the present invention preferably includes: a removable, high capacity, primary battery; a headphone/headset jack to support voice recognition applications. Moreover, preferably, the apparatus of the present invention includes, but is not limited to: a built-in microphone and speaker for easy recording; an accessory keyboard for entry of text and numerical information and a USB cradle for USB communications/interface to other devices and a battery charging function.

Figure 1:
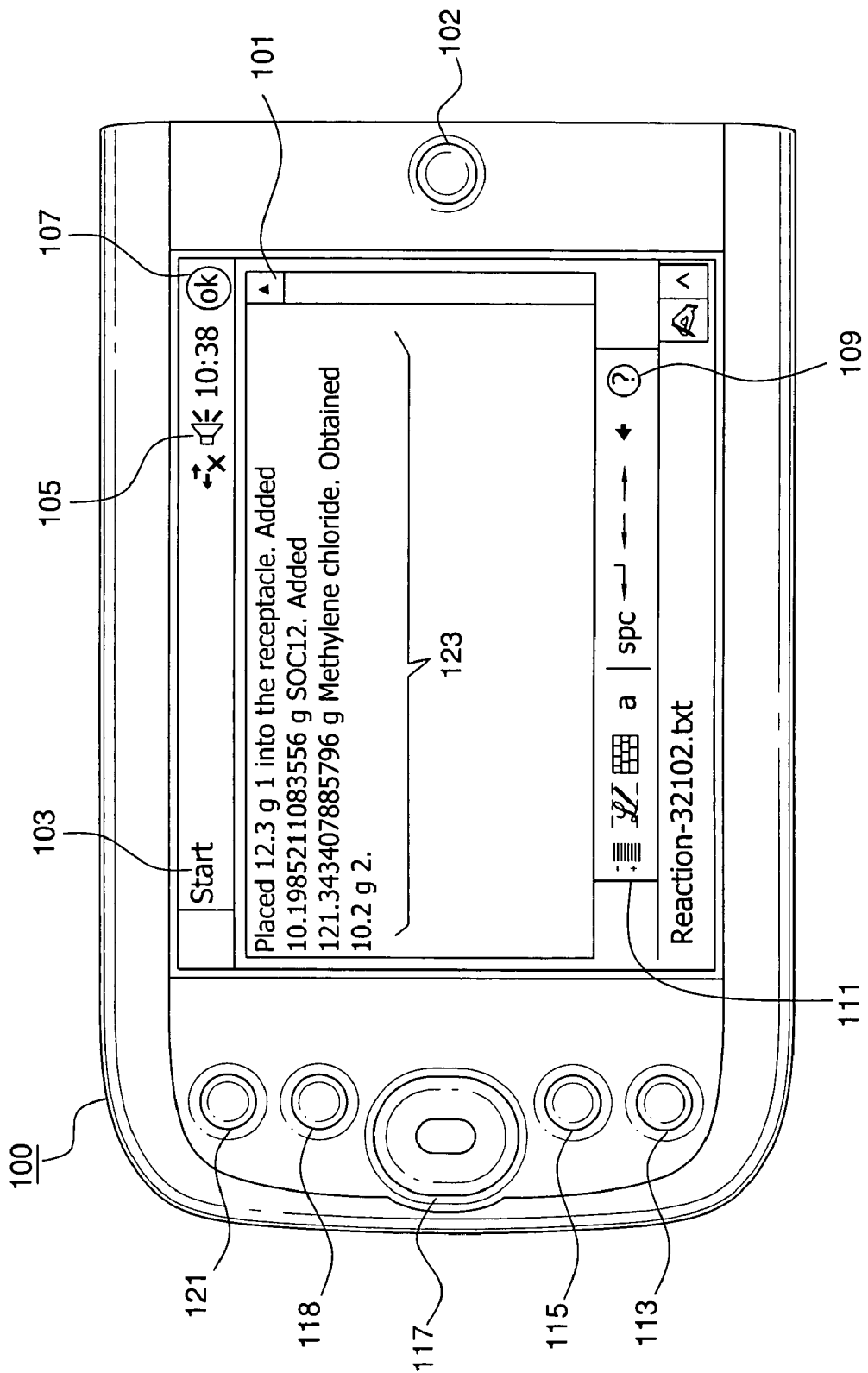
FIG. 1 is an exemplary frontal view of the apparatus illustrating data capture and text generation capabilities of the present invention.

FIG. 1 an exemplary frontal view of the apparatus of the present invention. In particular, FIG. 1 illustrates an exemplary PDA 100 that may be employed in the present invention. The PDA 100 further comprises, but is not limited to: a touch screen display 101, touch screen menu bar 103, 105, 107 providing access to Windows Mobile functionality, and Soft Input Panel control bar 109 and 111. Shortcut keys 113, 115, 118, 121 and a navigation toggle button 117 provide the user with easy access to programs and changing selection between objects within a group (not shown) on the touch screen display 101, respectively. In addition, the navigation toggle button 117 provides a program/icon selection function when the navigation toggle button 117 is depressed while the desired program icon is selected. Alternatively, icons can be selected with a stylus or other object that can be used to activate the touch screen display 101. The shortcut keys 113, 115, 118, 121 may represent, but are not limited to Calendar, Contacts, Inbox, and Home functions, respectively.

In addition, FIG. 1 illustrates the data capture and text generation capabilities of the present invention. As can be seen in FIG. 1, graphical and numerical data and laboratory events associated with developing a chemical reaction have previously been entered and have been recorded by the apparatus and translated into English text. This text may be generated prior, during, and after the completion of a chemical reaction in the laboratory by at least one of: (1) recording graphical symbols of chemical structures entered on the PDA 100 display 101; (2) writing alphanumeric data entries for the chemical reaction on the PDA 100 display 101 with a stylus or other object; (3) attaching an external keyboard to the PDA 100, typing alphanumeric entries for notes and results for viewing on the PDA 100 display 101; and/or (4) accessing icon buttons representing chemical procedures from within the graphical or tabular displays; and following these events by invoking the software processing to produce a textual record 123 of the execution of the reaction in the laboratory, as shown in FIG. 1. In any of the above cases, the textual record 123 can be stored in the PDA 100 apparatus and later uploaded to a personal computer or other device for further processing and/or integrating notes and results to, for example, produce additional reports.

Figure 2A:
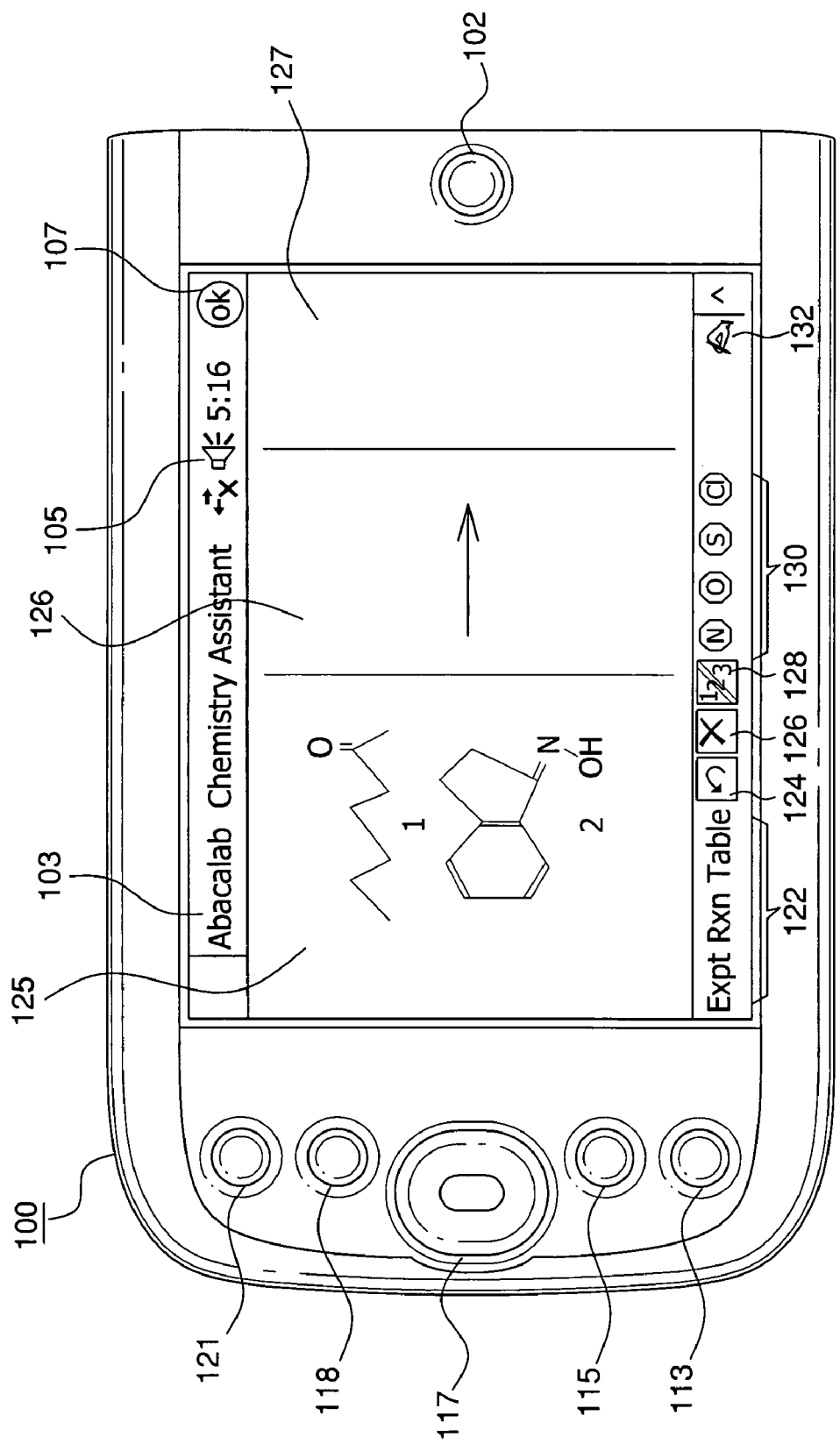
FIG. 2A is an exemplary frontal view of the apparatus illustrating the graphical interface capability of the present invention in the Viewing Mode.

FIG. 2A is an exemplary frontal view of the apparatus illustrating the graphical interface capability of the present invention in the "Viewing Mode." As can be seen in FIG. 2A, graphical and alphanumeric images are displayed on the display screen 101 in a format consistent with that traditionally used to represent chemical reactions. The display screen 101 is divided into three sections: a reactant area 125; a reagent area 126 and a product area 127. In addition to the controls described in FIG. 1, a number of addition control button are provided at the bottom of the display screen shown in FIG. 2A. These controls include, but are not limited to: pop-up menus 122, undo button 124, delete button 126, set bond types button 128, set atom to element buttons 130. The above discussed controls/buttons provide the standard functionality as indicated except as further discussed below.

The graphical representation of the reaction thus displayed can be generated by at least one of the following methods: (1) sketching the bonds of the structure as lines on the touch screen with a stylus or other object, using the standard conventions of structure drawing in organic chemistry in the reactant area of the display 125; (2) selecting the bonds of the structure (e.g., by pointing with the stylus or other object) and modifying them by selecting the set bond type buttons 128; (3) selecting the atoms of the structure (e.g., by pointing with the stylus or other object) and modifying them by selecting the atom type buttons 130; (4) selecting the atoms of the structure (e.g., by pointing with the stylus or other object) and modifying them by entering an element symbol using at least one of an attached keyboard, screen-based keyboard or handwriting recognition of an element symbol 132, pop-up menus 122; (5) selecting the atoms of the structure (e.g., by pointing with the stylus or other object) and modifying them by entering a functional group identifier using at least one of an attached keyboard, screen-based keyboard or handwriting recognition of an element symbol 132, pop-up menus 122; (6) selecting an atom, a bond, or an entire structure (e.g., by pointing with the stylus or other object) and deleting it by selecting the delete button 126; (7) selecting a chemical structure from a database by searching for it by an identifier, which may include, but is not limited to its proper name or its colloquial name using at least one of an attached keyboard, screen-based keyboard or handwriting recognition of an element symbol 132, pop-up menus 122; and (8) creating a copy of a structure for further modification by selecting a menu item for that purpose with the pop-up menus 122.

Using the tools described above, atoms may be assigned types corresponding with the elements of the periodic table, including also types representing commonly-used element isotopes such as deuterium. Functional groups, such as azide, carboxylic acid, nitro, or phenyl, can be specified by identifying them with commonly-used shorthand or with their partial molecular formulae.

In any of the above cases, the graphical records 125, 126, 127 or alphanumeric records can be stored in the memory of the PDA 100 apparatus and later uploaded to a personal computer or other device for further processing and/or integrating into, for example, a document or final report. Alternatively, the implementation discussed above can be performed on a personal computer or other programmable device.

Figure 3:
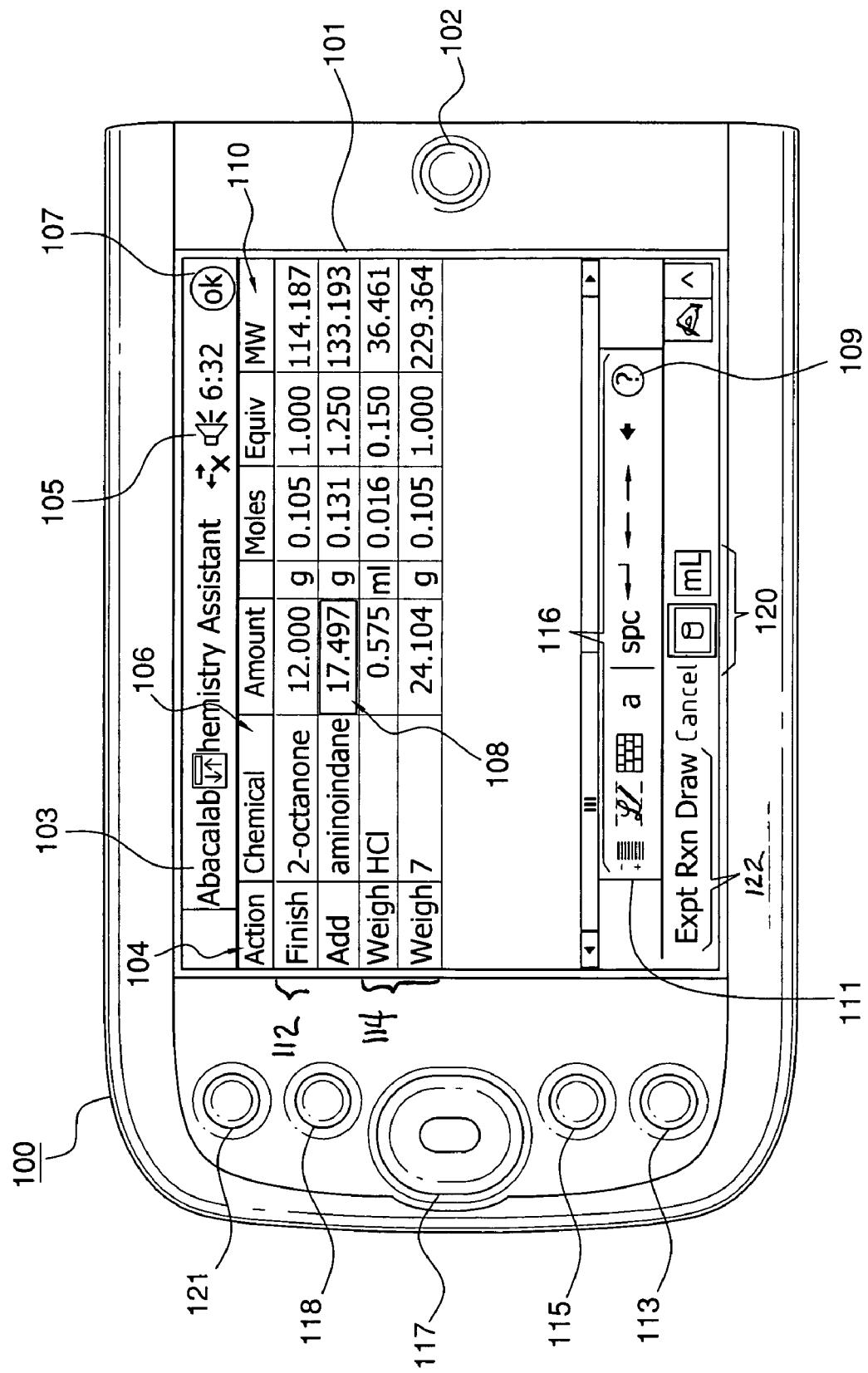
FIG. 3 is an exemplary frontal view of the apparatus of the present invention illustrating the numerical data entry and chemical calculation capabilities of the present invention.

FIG. 3 is an exemplary frontal view of the apparatus illustrating the tabular alphanumeric interface capability of the present invention. As can be seen in FIG. 3, alphanumeric data pertaining to the chemicals involved in a reaction are displayed on the screen in tabular form 128, with one row of the table pertaining to each chemical used or produced in the reaction. As can be seen in FIG. 3, notes or alphanumeric records 128 associated with developing a chemical structure/reaction and the results produced have been recorded on the display 101. The columns of the alphanumeric records 128 include, but are not limited to: experimental activity buttons 104; the alphanumeric chemical name 106, the amount of chemical 108, and the moles, equivalent and molecular weight of the chemical 110. The rows of these alphanumeric records 128 include one row for each chemical used or generated in the reaction, and may be classified as rows containing measured information 112 and rows with predetermined/planned information 114.

Alphanumeric data that is originated by the chemist either by design or by measurement can be entered into the apparatus with the stylus either by using controls of the handwriting recognition 116 or by an on-screen keyboard (not shown), or with an attached external keyboard. The handwriting recognition controls provide a human-machine interface that allows the conversion of the touch screen inputs by the chemist of the symbols of a chemical structure or reaction into graphical symbols for these structures and reactions on the screen of the device that can be interpreted by the apparatus of the present invention.

After the chemist enters the chemical structure into the apparatus, resultant data are computed from the data entered by the chemist with the standard formulae associated with chemical reactions, including but not limited to: (1) Molecular weight computed from the structure entered by the user in the drawing mode; (2) Molecular weight computed from the molecular formula entered as text; (3) Molecular weight of chemicals without meaningful formulae entered as numeric data; (4) Amount in grams of a chemical computed from the molecular weight and number of moles; (5) Amount in moles of a chemical computed from the molecular weight and number of grams; (6) Amount in moles of one chemical computed from the amount in moles of another chemical and the ratio of the two chemicals; and (7) Ratio of two chemicals computed from the amount in moles of each chemical.

As can also be seen in FIG. 3, different rows of the table are treated differently with respect to display and with respect to computation depending on whether the amount pertaining to the respective row is an amount planned by the chemist or an amount actually measured. Furthermore, as can be seen in FIG. 3, information pertaining to the measurement and addition of chemicals to the reaction can be conveniently entered by the chemist into the tabular alphanumeric display by tapping the buttons associated with each table row using the stylus or other object.

FIG. 3 also illustrates a cell 108 on the display screen 101 for numeric entry; pop-up menu buttons 118 and measurement unit buttons 120 (e.g., grams (g), milliliters (ml), etc). Moreover, each of FIG. 1 to FIG. 4 illustrate a soft input panel control button 132 that invokes an on-screen keyboard and/or handwriting recognition functions. It should be also be noted that, an alternative apparatus to the implementation discussed above can also be provided in the form of a personal computer or other programmable device capable of performing the methods of the present inventions.

In the present invention, when possible, the user is provided with the maximum possible active drawing space on the touch-sensitive display screen while still displaying drawing components that are not being edited. This capability is achieved by having those portions of the drawing that are not actively being edited relocated to provide additional space as the active editing object requires, thus reducing visual distraction, and also by rendering inactive objects transparent to certain pointer events, thus enabling use of the entire display for many drawing operations regardless of whether it occupied by inactive objects. At the same time, the active editing object itself must not be moved while the user is actually engaged in drawing it.

Figure 4:
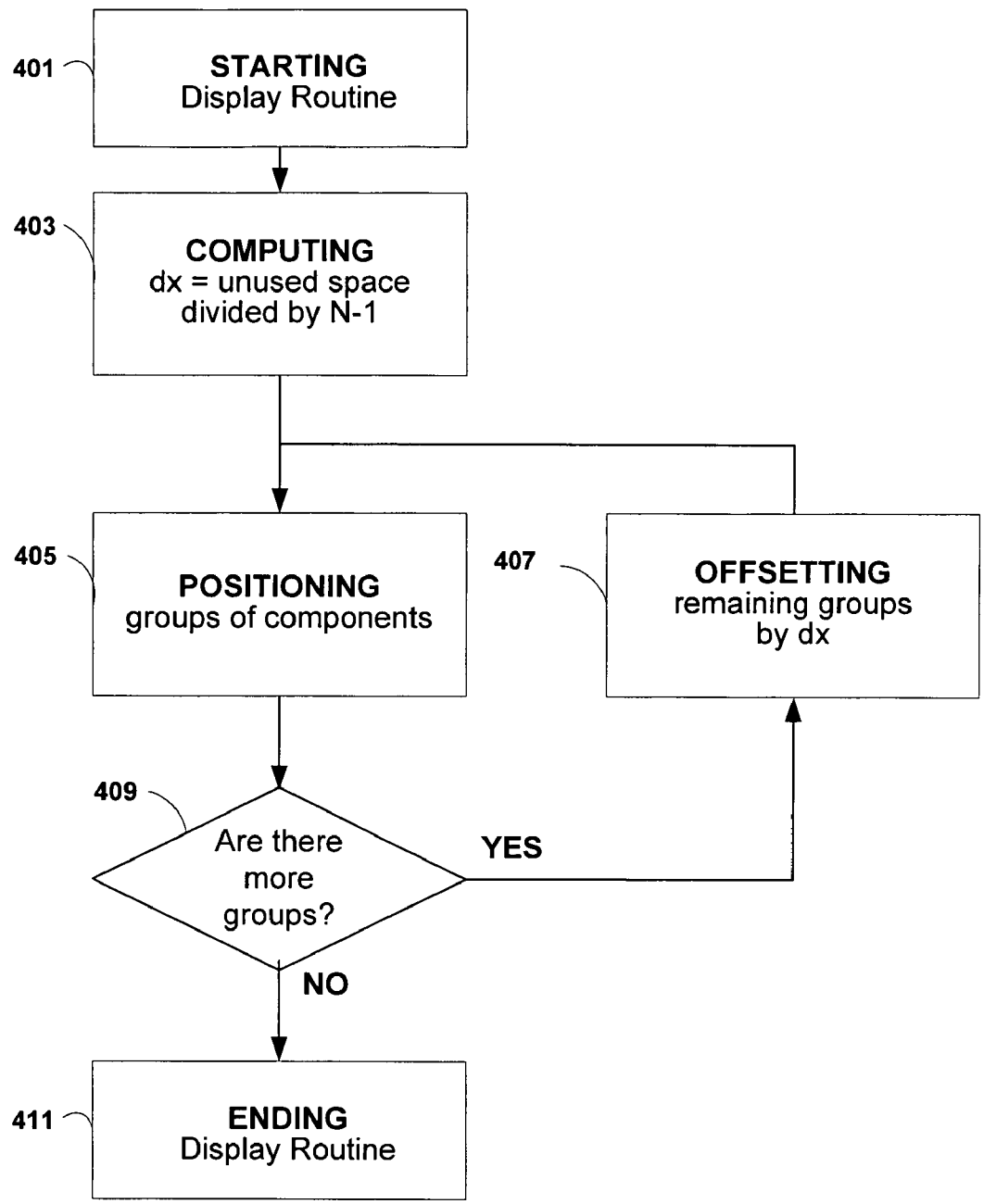
FIG. 4 is an exemplary flow diagram for a Display routine for a screen space management method of the present invention.

FIG. 4 is an exemplary flow diagram for a Display routine for a screen space management method of the present invention. In step 401 of FIG. 4, the Display routine is started. Computing the value of distance (dx), which is the unused space on the display screen divided by N−1, where N is the number of groups of components to be displayed, is performed in step 403. Step 405 is the positioning of groups of components. In step 409, the method determines whether there are more groups. If the answer is YES, than offsetting of the remaining groups is performed in step 407, which then returns to step 405. If the answer is NO, the Display routine ends at step 411.

When the user wishes to see or edit a graphical view of a reaction, the information is displayed in such a way that all of it fits onto the screen simultaneously while optimizing comprehensibility. Thus, the present invention includes separate modes for determining drawing component locations. These modes include, but are not limited to: a "Viewing Mode" and an "Editing Mode," as discussed below.

Figure 5:
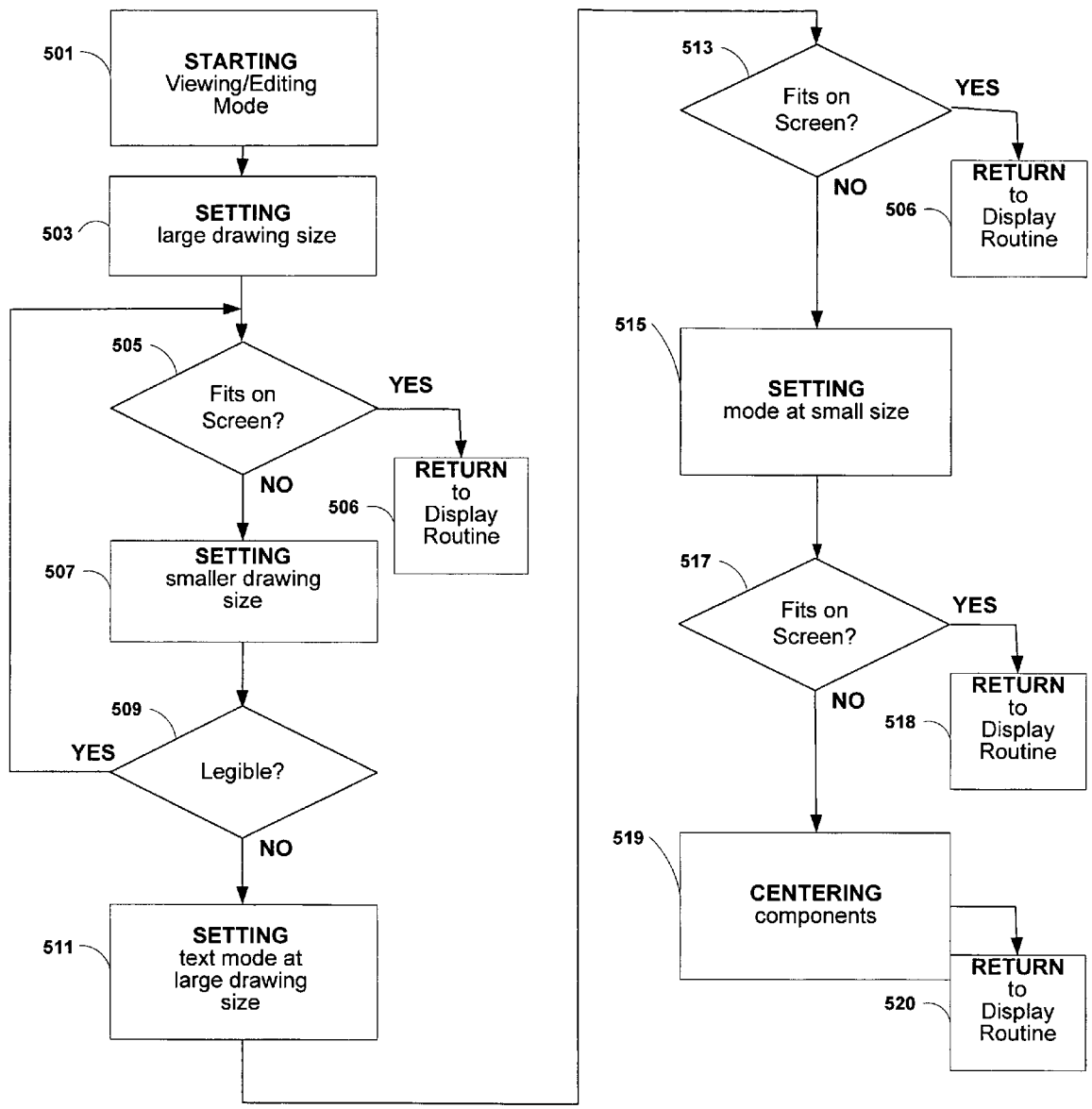
FIG. 5 is an exemplary flow diagram for a Viewing/Editing routine for method of the present invention.

FIG. 5 is an exemplary flow diagram for a Viewing Mode selection routine for the method of the present invention. In the "Viewing Mode," all components of the chemical reaction have an equal importance. Thus, the objective is to fit everything on the screen with equal prominence. In order to do this, the screen area is split into three conceptual areas: (1) Reactant area; (2) Reagent area; and (3) Product area, as shown in FIG. 2A discussed above. For the Viewing Mode, the components of the reaction being displayed are allocated into 'layout boxes' according to their role within the reaction. A reaction arrow is added to the Reagent area. The amount of space required for each component, and hence for each layout box, and thus for the entire reaction, is calculated.

In step 501 of FIG. 5, the Viewing Mode routine is started. An optimistic large drawing size is tried in step 503. The drawing size is described internally in terms of the average length of a chemical bond in the drawing. If in step 505, it is determined that all of the drawing objects can fit on the screen (i.e., YES), step 506 is executed and control is returned to the Display routine described above. Otherwise, the answer is NO and the drawing size is reduced in step 507 and this sequence is repeated until the drawing becomes illegible (i.e., legible=NO), as determined in step 509.

If the objects to be displayed will not fit on the screen when displayed as drawings at the smallest legible size in steps 505-509, the text mode is initially set in step 511. In step 513, whether or not the text rendering fits on the screen is determined. If the answer is YES, then a return to the Display Routine is executed in step 514. If, using text only, everything still does not fit (i.e., the answer is NO), the font size is reduced in step 515. Next, in step 517, it is determined if everything still does not fit. If the answer is YES, then a return to the Display Routine is executed in step 518. If the answer is NO, the smallest text rendering of the reaction is centered on the screen in step 519 in the hope that the information shown is enough for the chemist to view meaningful information and select components for editing in the Editing Mode routine discussed below. Finally, the method returns to the Display Routine in step 520.

After determining the smallest legible size in steps 505-509, the text mode is initially set in step 511. In step 513, whether or not the drawing fits on the screen is determined. If the answer is YES, then a return to the Display Routine is executed in step 506. If, using text only, everything still does not fit (i.e., the answer is NO), the font size is reduced in step 515. Next, in step 517, it is determined if everything still does not fit. If the answer is YES, then a return to the Display Routine is executed in step 518. If the answer is NO, the smallest text rendering of the reaction is centered on the screen in step 519 in the hope that the information shown is enough for the chemist to view meaningful information and select components for editing in the Editing Mode routine discussed below. Finally, the method returns to the Display Routine in step 520.

Figure 2B:
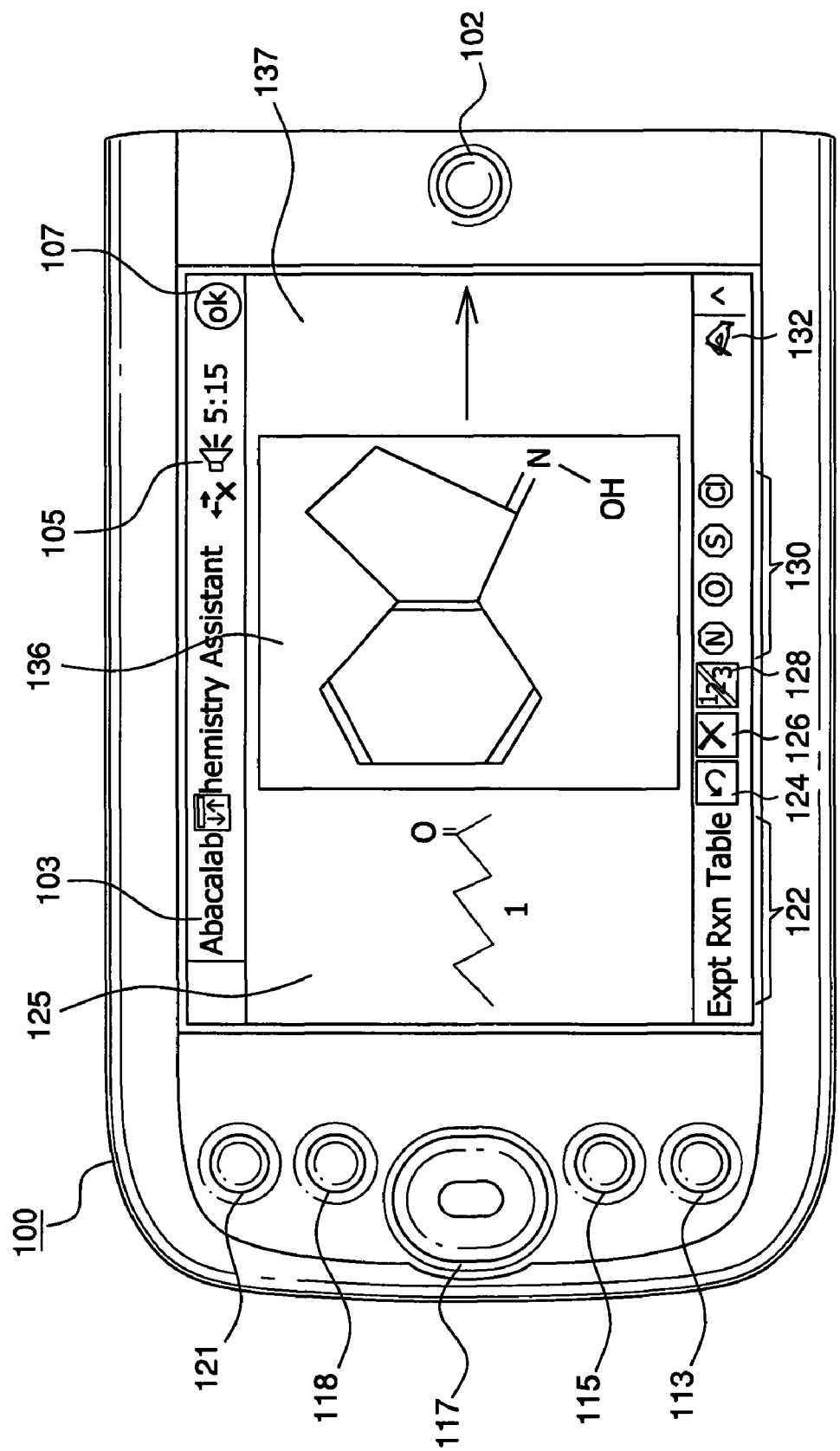
FIG. 2B is an exemplary frontal view of the apparatus illustrating the graphical interface capability of the present invention in the Editing Mode.

FIG. 2B is an exemplary frontal view of the apparatus illustrating the graphical interface capability of the present invention in the Editing Mode. In the "Editing Mode," if a reaction component is being edited, the positioning of drawing components on the screen is done such that the component being edited is given prominence greater than that of the other components. The method for choosing sizes for the non-editing components proceeds precisely as in the View Mode, discussed above.

In the Editing Mode, the display screen area 101 is split into four conceptual areas: (1) reactant area 125; (2) editing area 136; and (3) reagent area 137; and product area (not shown). The position of the "Editing area" is determined by the category of component being edited, and may be between the reactant area and the reagent area or between the reagent area and the product area. The drawing component in the Editing area is always displayed as a drawing (i.e., not text) and, if that size will fit on the screen, at its maximum size. If there is not enough space for the component being edited to be displayed at full size, smaller drawing sizes are tried. The components of the reaction being displayed are allocated into 'layout boxes' according to their role within the reaction. A Reaction arrow is added to the Reagent area. The amount of space required for each component, and hence for each layout box, and thus for the entire reaction, is calculated.

In addition to the controls described in FIG. 1, a number of addition control button are provided at the bottom of the display screen shown in FIG. 2B. These controls include, but are not limited to: pop-up menus 122, undo button 124, delete button 126, set bond types button 128, set atom to element buttons 130. The above discussed controls/buttons provide the standard functionality as indicated except as further discussed below.

The graphical representation of the reaction thus displayed can be edited by at least one of the following methods: (1) sketching the bonds of the structure as lines on the touch screen with a stylus or other object, using the standard conventions of structure drawing in organic chemistry in the reactant area of the display 125; (2) selecting the bonds of the structure (e.g., by pointing with the stylus or other object) and modifying them by selecting the set bond type buttons 128; (3) selecting the atoms of the structure (e.g., by pointing with the stylus or other object) and modifying them by selecting the atom type buttons 130; (4) selecting the atoms of the structure (e.g., by pointing with the stylus or other object) and modifying them by entering an element symbol using at least one of an attached keyboard, screen-based keyboard or handwriting recognition of an element symbol 132, pop-up menus 122; (5) selecting the atoms of the structure (e.g., by pointing with the stylus or other object) and modifying them by entering a functional group identifier using at least one of an attached keyboard, screen-based keyboard or handwriting recognition of an element symbol 132, pop-up menus 122; (6) selecting an atom, a bond, or an entire structure (e.g., by pointing with the stylus or other object) and deleting it by selecting the delete button 126; (7) selecting a chemical structure from a database by searching for it by an identifier, which may include, but is not limited to its proper name or its colloquial name using at least one of an attached keyboard, screen-based keyboard or handwriting recognition of an element symbol 132, pop-up menus 122; and (8) creating a copy of a structure for further modification by selecting a menu item for that purpose with the pop-up menus 122. Using the tools described, atoms may be assigned types corresponding with the elements of the periodic table, including also types representing commonly-used element isotopes such as deuterium. Functional groups, such as azide, carboxylic acid, nitro, or phenyl, can be specified by identifying them with commonly-used shorthand or with their partial molecular formulae.

A method for Automatic Reaction Role Determination in the present invention is now discussed. In drawing a chemical reaction, the various chemical substances in the chemical equation assume different roles in the reaction. Chemists ordinarily indicate these roles by the positioning of the symbols for these substances with respect to a reaction arrow. In order to perform computations, it is necessary for software to categorize these substances according to their role. Therefore, the method of the present invention contains an algorithm to determine the reaction role of a chemical substance automatically based upon where the user draws it with respect to the arrow on the screen. The screen location of newly created drawing objects is compared with that of the reaction arrow graphic: if a new object is to the left of the arrow it is identified as pertaining to a reactant; if it is to the right of the arrow it is identified as pertaining to a product; and if it is directly above or below the arrow it is identified as pertaining to a reagent.

The Automatic Capture of Procedural Information is discussed next. To facilitate the capture of information about the chemical procedures being performed in the laboratory, the method of the present invention interprets the laboratory activity implied by certain events that take place in the user interface (e.g., entry of the numerical values of particular measurements). The typical desktop-based drawing tools of the background art have a palette of tools that modify the behavior of the pointer (e.g. normal drawing, select, different bond types). In contrast to the background art, the present invention implements a paradigm where the pointer behavior does not change. Instead, different drawing effects are obtained by pointer gestures and by selecting buttons that modify a selected portion of the drawing. This approach is further detailed in the following paragraph.

The typical desktop-based drawing tools of the background art have a palette of tools that modify the behavior of the pointer (e.g. normal drawing, select, different bond types). In contrast to the background art, the present invention implements a paradigm where the pointer behavior does not change. Instead, different drawing effects are obtained by pointer gestures and by selecting buttons that modify a selected portion of the drawing. This approach is further detailed in the following paragraph.

Figure 6:
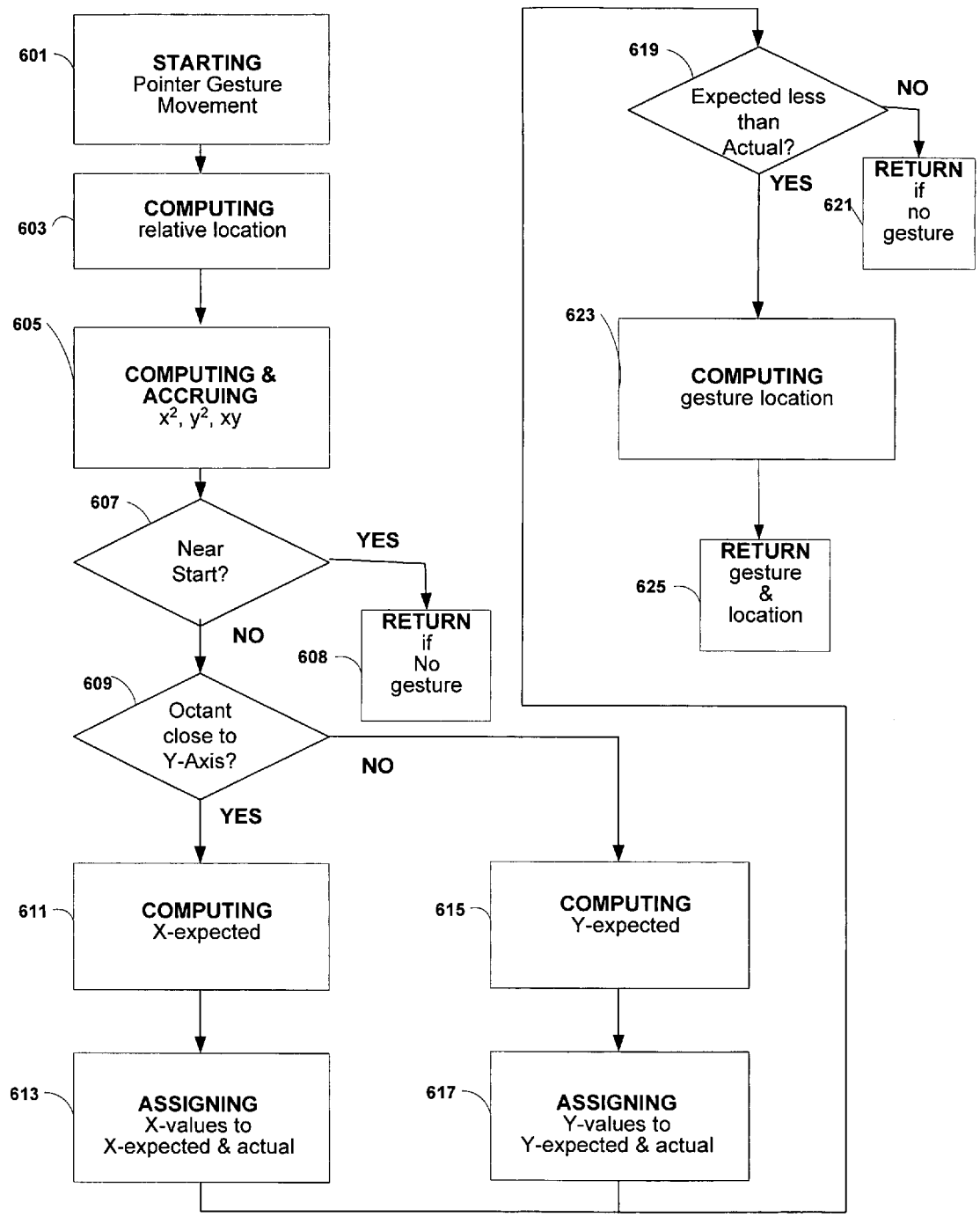
FIG. 6 is an exemplary flow diagram for Pointer Gesture movement routine for a gesture space management method of the present invention.

FIG. 6 is an exemplary flow diagram for a routine for a pointer gesture detection method of the present invention. In the handheld environment, it is important to interpret semantic content in a string of pointer movement events (i.e., pointer gestures) in the absence of interruption by pointer up and pointer down events; for example, the stylus may be applied to the screen and moved in a zigzag or circle before it is lifted from the screen, and it is desirable to interpret the series of screen coordinates associated with the pointer motion events as a gesture with a particular chemical meaning. An excellent example of this concept pertaining to a chemical structure is the interpretation of a pointer drag in a polygonal shape as representing a cyclic molecule with atoms at each vertex; for example the chemist would move the pointer in a square on the screen to represent cyclobutane.

In step 601 of FIG. 6, the pointer routine is started. Computing the relative location of the pointer is performed in step 603. Step 605 computes and accrues the values of $x^2$, $y^2$ and xy. In step 607, it is determined whether the pointer is near the start. If the answer is YES, then a RETURN to the calling routine is performed in step 608. If the answer is NO, step 609 determines whether the octant is close to the Y-Axis. If the answer is YES, computing X-expected and assigning X-values to X-expected/X-actual is performed in step 611 and step 613, respectively. If the answer is NO, step 609 determines whether the octant is close to the Y-Axis. If the answer is NO, computing Y-expected and assigning Y-values to Y-expected Y-actual is performed in step 615 and step 617, respectively.

Next, in step 619, it is determined whether the expected values are less than the actual values. If the answer is NO, there is no pointer gesture and a RETURN to the calling routine occurs in step 621. If the answer is YES, computing the location of the pointer gesture is performed in step 623. Finally, step 619 returns to the calling routine the pointer gesture and location.

Figure 7:
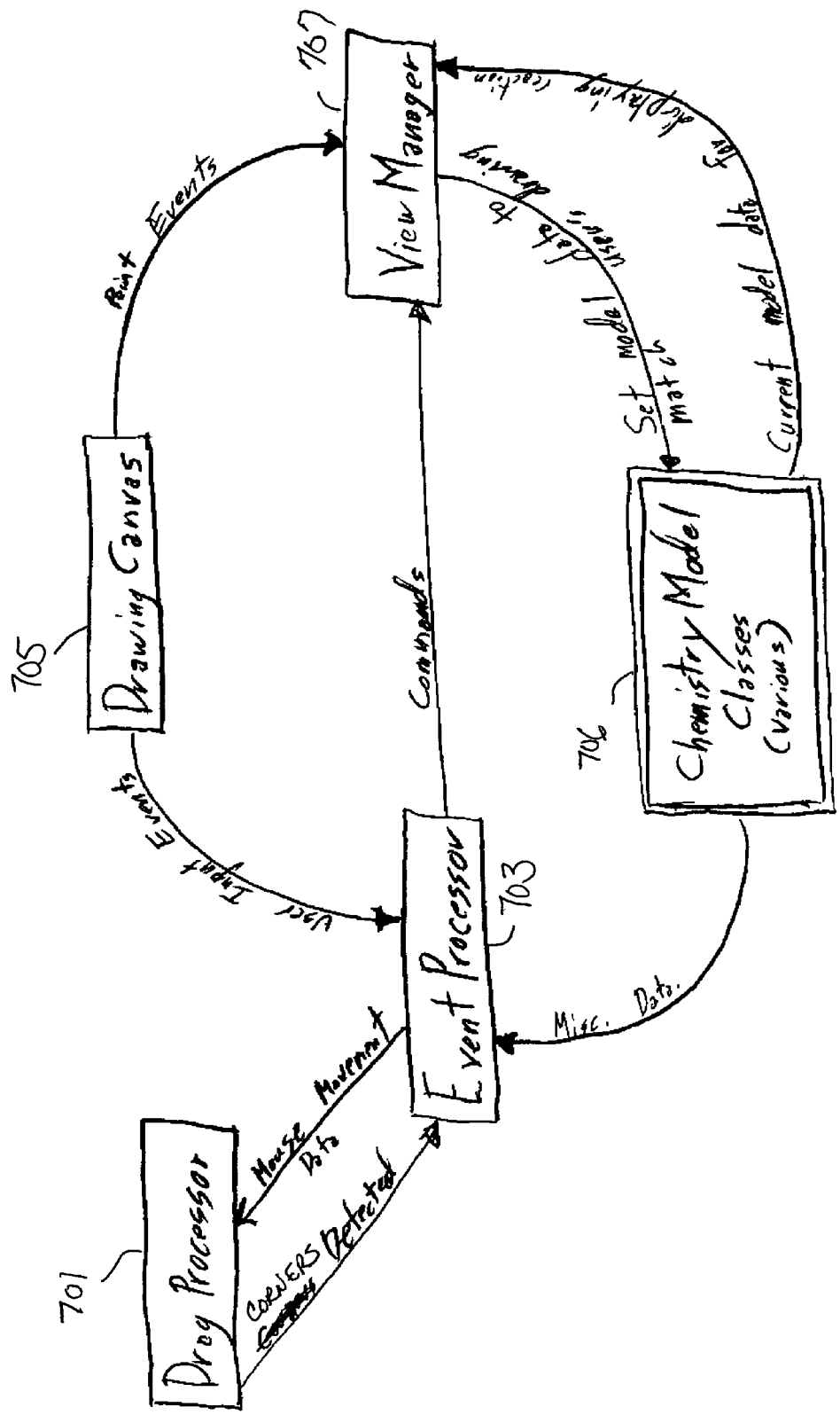
FIG. 7 is an exemplary class diagram for the present invention.

FIG. 7 is an exemplary class diagram for the present invention. All of the routines in the event flow diagram are part of a chemical drawing software package developed as a part of a software suite that embodies the present invention. In particular, the Display routines in FIG. 4 and FIG. 5 are part of the ViewManager class (i.e., in class diagram) and its helper classes, and are represented by the ViewManager column in the event flow diagram of FIG. 8. The gesture recognition routines in FIG. 6 are the greater part of the DragProcessor class as represented in both the class diagram and the event flow diagram of FIG. 7 and FIG. 8.

In particular, FIG. 7 shows the interconnection of a Drag Processor 701, Event Processor 703, Drawing Canvas 705, View Manager 707 and Chemistry Model Classes 706. As shown in FIG. 7, the Drag Processor 701 sends corners detected to the Event Processor 703 and receives Mouse Movement Data from the Event Processor 703. The Event Processor 703 receives Miscellaneous Data from the Chemistry Model Classes 706 and User Input Events from the Drawing Canvas 705. The Event Processor 703 sends Commands to the View Manager 707.

In addition, FIG. 7 shows the Drawing Canvas 705 sends point gesture events to the View Manager 707. The View Manager 707 send sends set model data to match the user's drawing to the Chemistry Model Classes 706. The Chemistry Model Classes 706 sends current model data for displaying the reaction to the View Manager 707.

Figure 8:
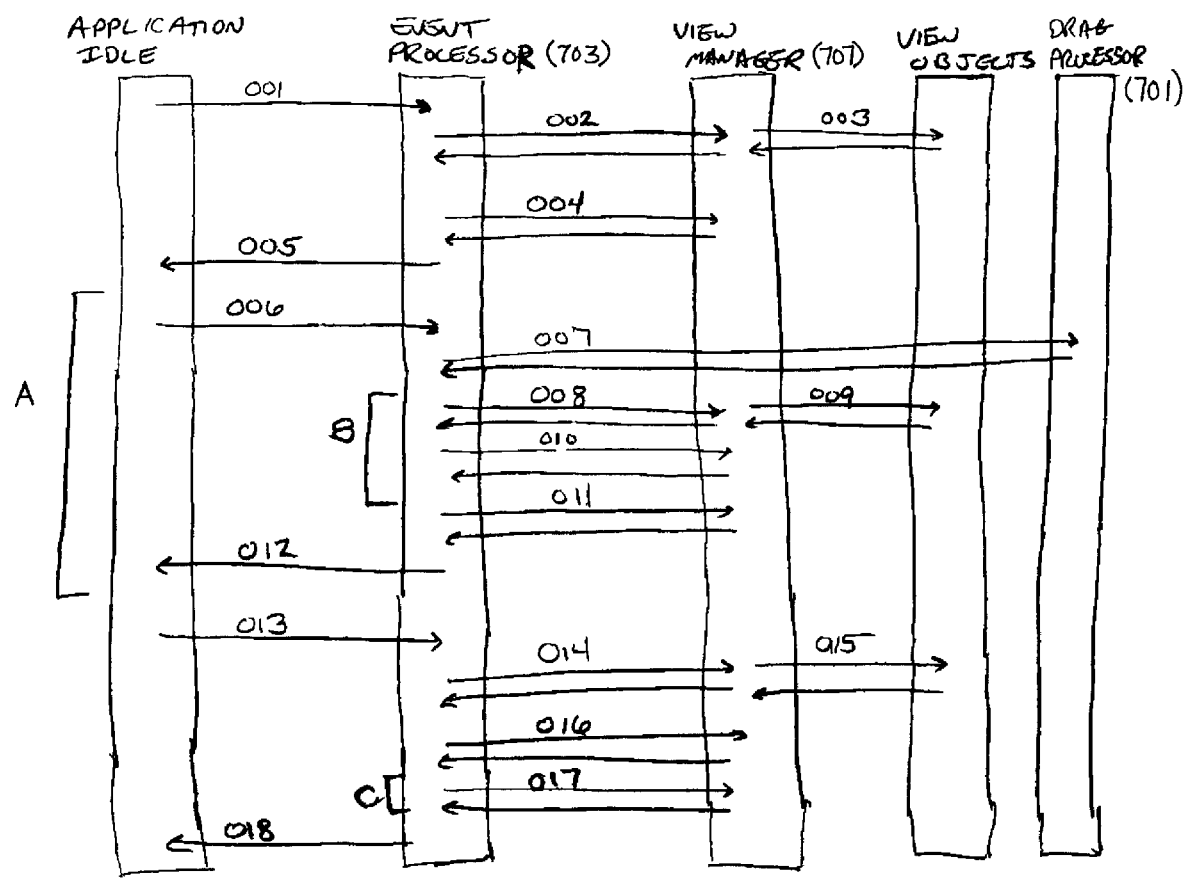
FIG. 8 is an exemplary event flow diagram for the present invention.

An event flow diagram for the present invention is shown in FIG. 8. The block of events enclosed by bracket A of FIG. 8 are repeated as many times as there are MouseMove events between the MouseDown and MouseUp. The block of events enclosed by bracket B of FIG. 8 is executed conditionally only when a pointer gesture is recognized by the DragProcessor. The block of events enclosed by bracket C of FIG. 8 are executed conditionally only when the user has exercised the pointer outside the area occupied by the chemical structure being actively edited. The Commands issued by the EventProcessor as a result of a MouseDown event at a point containing a specific kind of IViewObject (i.e., start of event 004 of FIG. 8) are different from those issued as a result of a pointer gesture recognition (i.e., start of event 010 of FIG. 8). Thus, it is possible for drawing objects to behave differently with pointer taps than when the pointer is dragged across them in a pointer gesture.

When the ViewManager determines the active IViewObject at a particular screen location, objects that are in Viewing Mode are processed differently than those in Editing Mode. The former can be returned only as entire chemical structures to the EventProcessor, whilst the individual components (e.g., bonds and atoms) of the latter can be returned, thus enabling access to editing events that affect them.

The commands issued by the EventProcessor to the ViewManager include instructions/commands for a variety of manipulations and editing tasks that include, but are not limited to: commands to manipulate atoms (e.g., represented by Nodes in the software) including, but not limited to: AddNodeCommand, DeleteNodeCommand, ElementChangeCommand, and FormalChargeChangeCommand; commands to manipulate bonds (e.g., represented by Connectors in the software), including, but not limited to: AddConnectorCommand, DeleteConnectorCommand, BondOrderIncrementCommand, and BondOrderDecrementCommand; including, but not limited to: commands to manipulate entire chemical structures (represented by Clusters in the software), including, but not limited to: AddClusterCommand, AddReagentClusterCommand, DeleteClusterCommand, NameClusterCommand, NicknameClusterCommand, and ChangeRoleClusterCommand; commands that manipulate the entire drawing or any type of object upon it, including, but not limited to: SelectCommand, DeleteSelectedCommand, CopyReactantsToProductsCommand, LayoutCommand, UndoLayoutCommand; and commands that provide infrastructure for the manipulation of the Commands themselves, including, but not limited to: FailedCommand and CompositeCommand.

In FIG. 8, event 001 is the receipt of a MouseDown event and Cache screen location. Event 002 of FIG. 8 is where the ViewManager determines whether an editable object is at a particular location. In event 003, iteration through currently displayed IViewObjects is performed. Event 004 is where the View Manager processes command(s) sent by the EventProcessor as a result of MouseDown event. Event 005 is a Return to idle loop and event 006 is the receipt of a MouseMove event. In event 007, pointer gesture recognition processing is performed by the Drag Processor. In event 008, iViewManager determines whether an editable object is at a particular location. In event 009, an iteration through currently displayed IViewObjects. In event 010, the ViewManager processes Command(s) sent by the EventProcessor as a result of a pointer gesture recognition. Event 011 is where the ViewManager update screen highlights as a result of MouseMove event. Event 012 is a Return to the idle loop. In event 013, a receipt of MouseUp event occurs. Event 014 is where the ViewManager determines editable object at a particular location. In event 015, Iteration through currently displayed IViewObjects occurs. Event 016 is where ViewManager processes Command(s) sent by EventProcessor as a result of MouseUp event. In event 017, the ViewManager executes display selection and display routines as initiated by the EventProcessor and event 018 is a Return to idle loop.

The foregoing description of the invention illustrates and describes the present invention. Additionally, the disclosure shows and describes only the preferred embodiments of the invention in the context of a method for increasing the yield of programmable logic devices, but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described herein above are further intended to explain best modes known of practicing the invention and to enable others skilled in the art to utilize the invention in such, or other, embodiments and with the various modifications required by the particular applications or uses of the invention. Accordingly, the description is not intended to limit the invention to the form or application disclosed herein. Also, it is intended that the appended claims be construed to include alternative embodiments.

What is claimed as new and desired to be protected by Letters Patent of the United States is:

1. An apparatus for display and analysis of chemical structures, comprising:
   a computing device, said computing device further comprising an operating system, chemical reaction software, graphical interface software, a plurality of types of memory and means for interfacing the computing device to a plurality of external devices;
   a display configured to provide icon fields;
   a touch-sensitive display area and stylus for the graphical input of chemical information;
   a plurality of shortcut keys; and
   a navigation toggle button configured to provide easy access to the software and to control the selection of various items on the touch screen display,
   wherein the computing device is configured to control the software, display, plurality of shortcut keys, and navigation toggle in completing and analyzing a chemical reaction, and
   wherein one of the operating system or the chemical reaction software is configured to display the chemical reaction in its entirety on the touch-sensitive display area during an editing mode, the chemical reaction including a primary chemical reaction element, which is displayed within a first portion of the touch-sensitive display area, and a plurality of secondary chemical reaction elements, which are displayed outside of the first portion of the touch-sensitive display area, and to accept editing input outside the first portion of the touch-sensitive display area for editing the primary element during display of the chemical reaction in its entirety.

2. The apparatus of claim 1, wherein
   alphanumeric data pertaining to the chemicals involved in a reaction are displayed on the display screen in tabular form with one row of the table pertaining to each chemical used or produced in the reaction,
   alphanumeric records associated with developing a chemical structure/reaction and the results produced have been recorded on the display screen,
   columns of the alphanumeric records include experimental activity buttons; the alphanumeric chemical name, the amount of chemical, and the moles, equivalent and molecular weight of the chemical, and
   rows of these alphanumeric records include one row for each chemical used or generated in the reaction and are classified as rows containing measured information and rows with predetermined/planned information.

3. The apparatus of claim 1, wherein one of the operating system or the chemical reaction software is further configured to repeatedly reduce a display size of at least the secondary elements of the chemical reaction until all the elements are displayed on the touch-sensitive display area simultaneously.

4. The apparatus of claim 3, wherein repeatedly reducing the display size of at least the secondary elements of the chemical reaction includes substituting textual elements for graphical elements.

5. The apparatus of claim 3, wherein repeatedly reducing the display size of at least the secondary elements of the chemical reaction includes reducing a font size of displayed textual elements.

6. The apparatus of claim 3, wherein repeatedly reducing the display size of at least the secondary elements of the chemical reaction includes allotting equal space on the touch-sensitive display area for each of the reduced elements of the chemical reaction.

7. The apparatus of claim 3, wherein repeatedly reducing the display size of elements of the chemical reaction includes not reducing the display size of the primary element.

* * * * *